US00PP12617P2

(12) United States Plant Patent
Yates

(10) Patent No.: US PP12,617 P2
(45) Date of Patent: May 7, 2002

(54) JAMESBRITTENIA PLANT NAMED 'YAGEVI'

(76) Inventor: Frederic Yates, Poplar Nursery Holmes Chapel Rd., Somerford, Congleton, Cheshire, CW12 4FP (GB)

( * ) Notice: Subject to any disclaimer, the term of this patent is extended or adjusted under 35 U.S.C. 154(b) by 0 days.

(21) Appl. No.: 09/689,324

(22) Filed: Oct. 12, 2000

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Mark P. Bourgeois

(57) ABSTRACT

A new Jamesbrittenia plant named 'Yagevi', that is characterized by unique violet colored flowers, and small leaves that are marginally lobed. These combined traits set it apart from all existing varieties in the trade known to the inventor.

2 Drawing Sheets

CROSS-REFERENCES TO RELATED APPLICATIONS

This application corresponds to two other applications entitled Jamesbrittenia Plant Named 'Yagero' (U.S. patent application Ser. No. 09/689,332) and Jamesbrittenia Plant Named 'Yagepin' (U.S. patent application Ser. No. 09/689,327), both of which have the same inventor and filing date as the present invention.

BACKGROUND OF THE INVENTION

The present invention relates to a new and distinct cultivar known botanically as a Jamesbrittenia of hybrid origin and referred to hereinafter by the cultivar name 'Yagevi'. The genus Jamesbrittenia has been split from the genus Sutera under which plants of Jamesbrittenia have hitherto been classified.

The new plant 'Yagevi' was bred and selected from a long term breeding program aimed at producing new forms and colors of hanging baskets and patio plants. The exact parents of 'Yagevi' are unidentified Jamesbrittenia species hybrids. The original breeding material included Jamesbrittenia species *jurassica, breviflora, microphylla* and *pristisepala*, (none of these are patented). Through open pollination the species hybridized producing many generations of seedlings. From these seedlings that resulted from various unidentified crosses of Jamesbrittenia species, four new selections were made. The breeding program was conducted by the inventor in a culitvated area of Congleton, Chesire England. The inventor conducted first crosses in the summer of 1992 and made four selections in 1999, of which 'Yagevi' was one. The method of origination or breeding technique was seedling selection and re-selection, followed by asexual propagation using cuttings.

'Yagevi' was selected for its characteristics as a new hanging basket and can be distinguished as unique because of its leaf size, leaf shape and its flower color. The foliage resembles that of 'Yagepin' and 'Yagero' but the flower color of 'Yagevi' differs from them. Together the three varieties exhibit foliage that has smaller leaves that are marginally lobed, and differ from all other varieties in the trade. The closest comparison varieties to 'Yagevi' are 'Yagepin' with pink-colored flowers, and 'Yagero' with rose-colored flowers, while 'Yagevi' exhibits violet-colored flowers.

The first asexual propagtion was conducted by the inventor in Congleton, Chesire England in 1999. The new individual has been found to be stable through many cycles of vegetative propagation and remains true to type demonstrating no off-types.

SUMMARY OF THE INVENTION

The following traits have been repeatedly observed and represent the characteristics of the new cultivar. These attributes in combination distinguish the new invention from all other varieties known to the inventor. 'Yagevi' is a new selection of hanging basket, chosen for its flower color and the size and shape of its leaves. Although it resembles 'Yagero' and 'Yagepin' in foliage, the leaves are collectively smaller and maginally lobed in comparison to all other existing varieties. In flower color, 'Yagevi' in unique. Violet flowers distinguish 'Yagevi' from 'Yagepin' which exhibits pink flowers, and 'Yagero' which has rose flowers.

BRIEF DESCRIPTION OF THE DRAWINGS

The accompanying color photographs illustrate the overall appearance of the new cultivar.

Sheet 1 is a good representation of the overall plant form, foliage, and flower color.

Sheet 2 illustrates the flower and leaf from a close-up perspective. All photographs are taken of plants grown in one-gallon containers. The prints are made using conventional photographic techniques and although colors may appear different from actual colors due to light reflectance they are as accurate as possible by conventional photography.

BOTANICAL DESCRIPTION OF THE PLANT

The following is a detailed description of the new cultivar as grown in a one-gallon container under greenhouse conditions in Encinitas, Calif. Phenotypic differences may be observed with variations in environmental, climatic and cultural conditions, without however, any variance in genotype. Colour determinations are in accordance with The Royal Horticultural Society Colour Chart except where general color terms of ordinary dictionary significance are used.

Botanical classification: Jamesbrittenia 'Yagevi'.
Common name: Bacopa.
Use: Hanging basket, patio plant.
Parentage: The parents of 'Yagevi' are Jamesbrittenia species hybrids.
*Seed parent.*—Unidentified Jamesbrittenia species hybrid.
*Pollen parent.*—Unidentified Jamesbrittenia species hybrid.
Propagation: Vegetative cuttings.
Type: Annual.
Root system: Fibrous.
Seasonal interest: Floral display in spring and summer.
Special growing requirements: Shear after heavy flowering.
Cropping time: 8 weeks to root from cutting.
Diseases and pests: Potential for mildew.
Growth habit: Mounding, prostrate.
Plant shape: Projected, fountain-like.
Height: 35 cm. high.
Width: 60 cm. wide.
Hardiness: Observed as hardy from −5 to 10 degrees Centigrade, however hardiness has not been fully tested.
Soil: Free-draining.
Light levels: Plant in part shade to full sun.
Stem shape: Cylindrical.
Branching habit: Angular and cascading.
Stem color: 144A.
Stem size: 20–28 cm. long by 2 mm. wide.
Internode length: 0.50 to 1.5 cm. between nodes.
Stem surface: Pubescent with long and short hairs.
Foliage:
*Leaf arrangement.*—Alternate.
*Leaf division.*—Simple.
*Shape.*—Lyrate with shallow terminal lobes.
*Base.*—Acuminate.
*Apex.*—Retuse with two notches.
*Venation.*—Prominent mid-vein with secondary veins diverging to lobes.
*Margins.*—Pinnately lobed.
*Surface.*—Pubescent on upper and lower surfaces.
*Length.*—1 cm. long.
*Width.*—0.75 cm. wide.
*Young leaf color* (*upper surface*).—138A.
*Young leaf color* (*lower surface*).—138B.
*Mature leaf color* (*upper surface*).—137B.
*Mature leaf surface* (*lower surface*).—137C.
*Petiole length.*—4–5 mm. long.
*Petiole width.*—1 mm. wide.
*Petiole color.*—138B.
*Foliar fragrance.*—Slightly resinous to turpentine-like scent.
Flower:
*Type.*—Raceme.
*Shape.*—Circular, rotate.
*Quantity.*—Floriferous.
*Margins.*—Entire.
*Surface.*—Glabrous.
*Fragrance.*—None observed.
*Flower size.*—4 mm. high by 2 cm. in diameter.
*Flowering season.*—Spring and summer.
*Flowering time.*—Diurnal.
*Aspect.*—Marjority of flowers facing upward.
*Peduncle length.*—2.50 cm. long.
*Peduncle width.*—1 mm. wide.
*Peduncle color.*—144A.
*Persistent or non-persistent.*—Persistent.
*Petals.*—Five petals.
*Fused or unfused.*—Unfused.
*Petal color.*—81A opening, 80A mature.
*Unique features.*—Dark veins 79B around throat and moderately on petals.
*Other flower characteristics.*—Sunburst in throat 25A and exhibiting white 155D on one side of throat edge.
*Throat depth.*—4 mm. deep.
*Calyx.*—Heavily pubescent, stipitate glandular surface.
*Calyx size.*—3 mm. wide by 2.5 mm. high.
*Calyx color.*—144B.
*Sepal color.*—144B.
*Sepal width and length.*—3 mm. wide by 2.5 mm. long.
*Sepal number.*—Five.
Reproductive organs:
*Stamens.*—Two stamens.
*Stamen dimensions.*—6–7 mm. in length and 0.50 mm. in diameter.
*Pollen color.*—25A.
*Pistil color.*—144C.
*Number of pistils.*—One in number.
*Pistil dimensions.*—6.5–7.5 mm. in length and 0.75 mm. in diameter.
Seed production:
*Seed shape.*—Spherical in shape.
*Seed dimensions.*—0.60–0.75 mm. in diameter and 0.60–0.75 mm. in height.
*Seed color.*—199B.
*Capsule color.*—200A.
*Capsule dimensions.*—2.5 mm. in diameter and 6 mm. in length.
*Capsule shape.*—Ovate.
*Seed surface.*—Glabrous.
*Seed quantity.*—30–40 per capsule.

I claim:

1. A new and distinct cultivar of Jamesbrittenia plant named 'Yagevi' as described and illustrated.

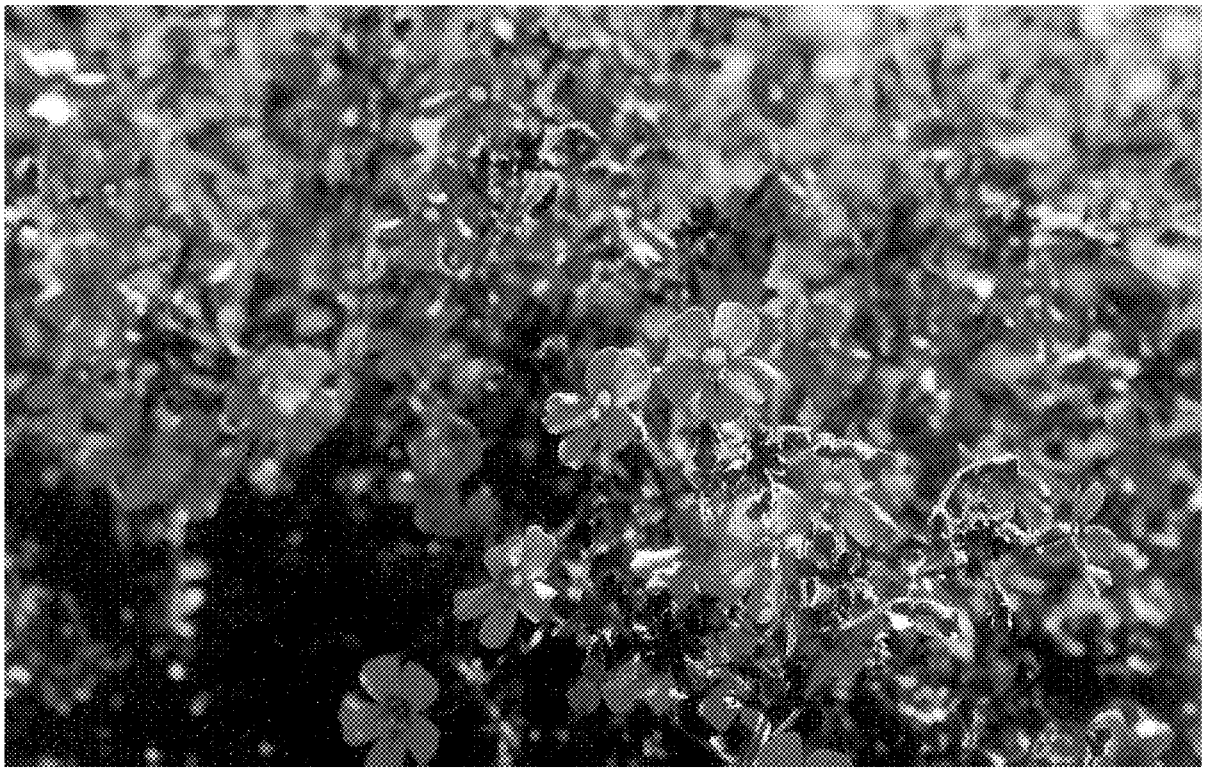

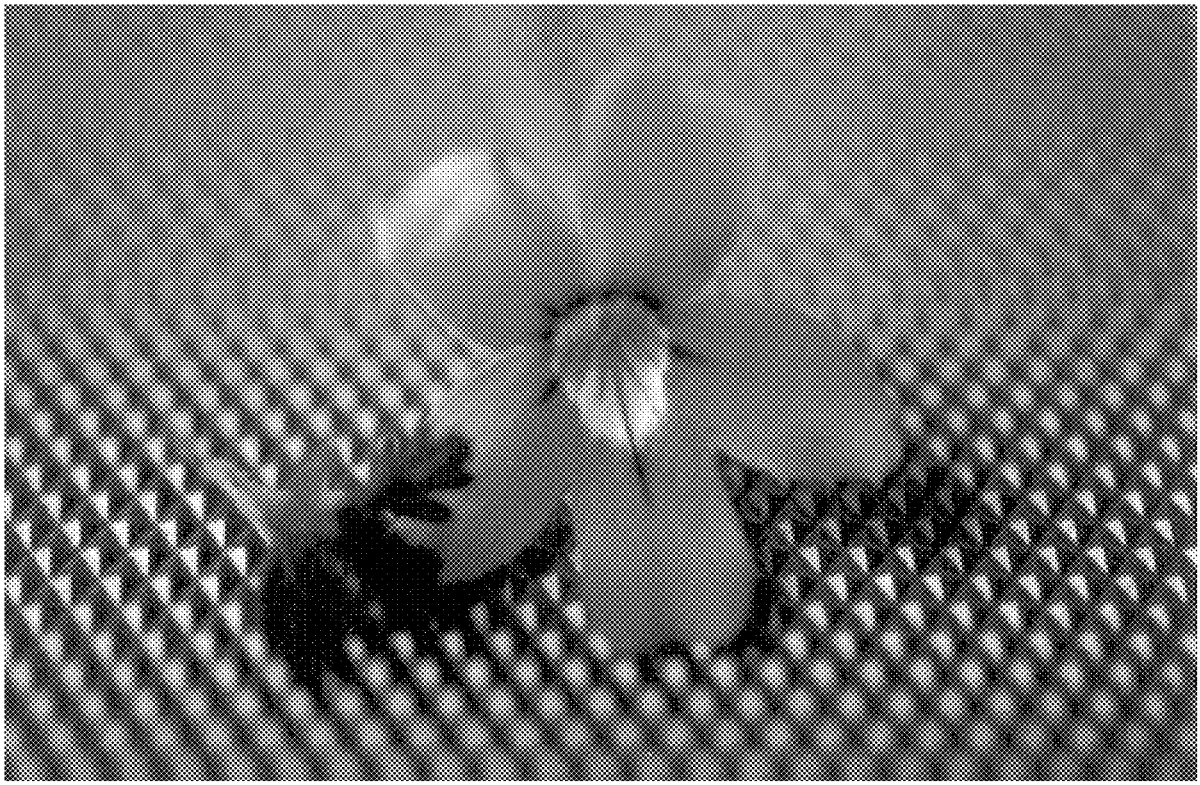

* * * * *